United States Patent [19]

Cole et al.

[11] 4,246,339
[45] Jan. 20, 1981

[54] TEST DEVICE

[75] Inventors: Francis X. Cole, Stowe; James H. Edwards, Winchester; Clifford L. Hendrick, Boxboro; Deborah M. VanVoorhis, Watertown, all of Mass.

[73] Assignee: Millipore Corporation, Bedford, Mass.

[21] Appl. No.: 956,702

[22] Filed: Nov. 1, 1978

[51] Int. Cl.³ .................. C12Q 1/66; C12M 1/00
[52] U.S. Cl. ........................... 435/7; 435/287; 23/230 B; 422/101; 422/102
[58] Field of Search .......... 435/7, 288, 291, 287; 424/12; 23/230 B; 422/69, 71, 61, 101, 102

[56] References Cited

U.S. PATENT DOCUMENTS

| 3,990,852 | 11/1976 | Piazzi et al. | 435/7 |
| 4,066,512 | 1/1978 | Lai et al. | 435/291 |
| 4,090,850 | 5/1978 | Chen et al. | 23/230 B |
| 4,111,754 | 9/1978 | Park | 435/7 |
| 4,146,365 | 3/1979 | Kay et al. | 23/230 B |

Primary Examiner—Thomas G. Wiseman
Attorney, Agent, or Firm—Kenneth D. Hudson

[57] ABSTRACT

A test device for assaying liquid samples for the presence of a predetermined reagent is described. The device comprises telescoping top and bottom members defining a liquid reservoir therebetween, resilient means for biasing the members in the open position, one or more test wells in the top member with bottom openings covered with microporous membranes, a co-reactant immobilized on the membrane surfaces, and sorbent means between the members spaced from the membrane(s) in the open position but in contact therewith in the closed position. Liquids are passed through the membrane(s) into the sorbent means by depressing the members to the closed position.

12 Claims, 4 Drawing Figures

TEST DEVICE

BACKGROUND OF THE INVENTION

This invention relates to fluid test devices, and more particularly to test devices for testing biological fluids or the like for the presence of a diagnostic reagent.

Test procedures for assaying biological fluids using the specific reactivity of antibody-antigen pairs, enzyme-substrate pairs, and the like are known and are disclosed, for example, in U.S. Pat. Nos. 3,770,380; 3,839,153; 3,951,748; 4,002,532. Commonly, the co-reactant is fixed or immobilized to the surface of a support and the liquid sample containing or suspected of containing the reagent is brought into contact therewith and allowed to react, the presence of specific reaction product being monitored to infer the presence of reagent in the sample. For biological liquids such as serum, urine, CSF, peritoneal exudates, or the like, E.L.I.S.A. (enzyme-linked immuno-sorbent assay), R.I.A. (radio immuno assay), or similar monitoring procedures may be used.

Microporous membranes provide a particularly desirable immobilizing support or carrier for biologically active materials and are described in U.S. Pat. No. 4,066,512. Test procedures using such supports are described in copending U.S. patent applications Ser. Nos. 751,093, abandoned, and 751,099, abandoned, respectively filed on Nov. 10, 1976 and Dec. 16, 1976. The disclosures of these references are herein incorporated by reference.

While these and other similar test procedures are known, considerable skill, equipment and time are often required in execution. A need therefore exists for a simple test device in which the tests can be conveniently and rapidly performed at any suitable location.

OBJECTS OF THE INVENTION

It is a principal object of the present invention to provide a simple and convenient test device for testing liquid samples for the presence of predetermined components. Further objects include provision of test devices which are portable, substantially self-contained, operable at room temperature, and in which a test membrane is mounted for ease and rapidity of exposure to sample, incubation, washing, and monitoring for reaction product, for example by E.L.I.S.A. techniques. Other and additional objects and advantages will be apparent from the following description.

SUMMARY OF THE INVENTION

The present invention provides a test device for assaying liquid samples such as biological fluids for the presence of a diagnostic reagent. The device comprises telescoping top and base members defining therebetween a liquid reservoir, the top member having one or more test wells each having a bottom opening to the periphery of which a microporous membrane is sealed, the membrane having fluid passages therethrough and having a co-reactant immobilized to its internal and external surfaces, resilient means biasing the members in the open position, and sorbent material in the reservoir between the members having an upper surface spaced from the membrane(s) in the open position and adapted to contact the membrane(s) in the depressed position. The liquid capacity of the sorbent material should be sufficient to absorb by blotting or capilliary action all the liquids to be passed through the wells. Preferably, a plurality of wells are provided sufficient for several tests, including positive and negative controls, and the sorbent material has an upper surface layer which is not wetted by the liquids passing through the wells to minimize re-wetting the membranes with previously used liquids.

In use, the liquid sample to be assayed is placed in a well, preferably covering the upper surface of the membrane, the membrane and sample are incubated for a time sufficient for reaction to occur between the sample reagent, if any, and the membrane co-reactant, and the top member is the depressed to pass the sample through the membrane into the sorbent material. The membrane may be washed to remove unreacted materials by relaxing the top member, placing wash liquid in the test well, and again depressing the top member to pass the wash liquid through the membrane into the sorbent material, repeating the washing steps, if desired.

Reaction product in the membrane, if any, can be shown by any suitable teachnique. For use with E.L.I.S.A. procedures when the reagent and co-reactant are a specific antibody-antigen pair, a conjugate of an active enzyme with a biological material specific to the harvested reagent can be passed through the membrane, followed by washing as above described. A substrate-chromogen mixture specific to the enzyme is then passed through the membrane to develop visible color in the presence of harvested reagent. Preferably the test is performed with positive and negative controls in which control samples, (a) known to contain the reagent (positive) and (b) known to be free of reagent (negative), are passed through adjacent test wells and the control membranes compared with the test membrane(s).

DESCRIPTION OF PREFERRED EMBODIMENTS

The preferred embodiment of the present invention is shown in the accompanying drawing in which.

Figure 1:
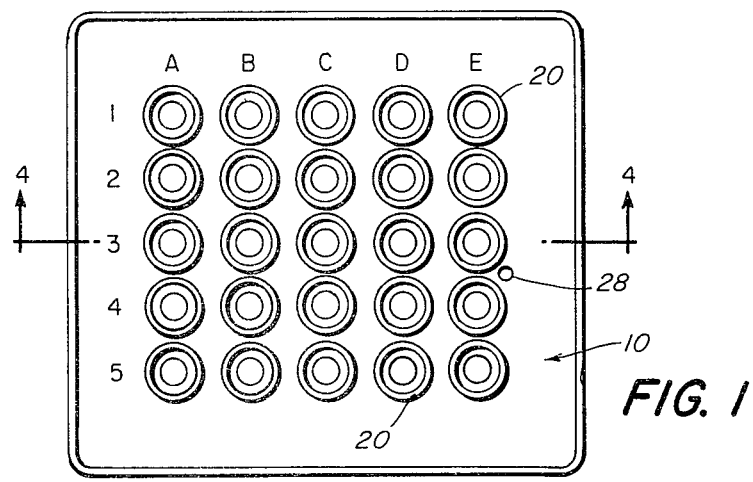
FIG. 1 is a top view of the test device.
Figure 2:
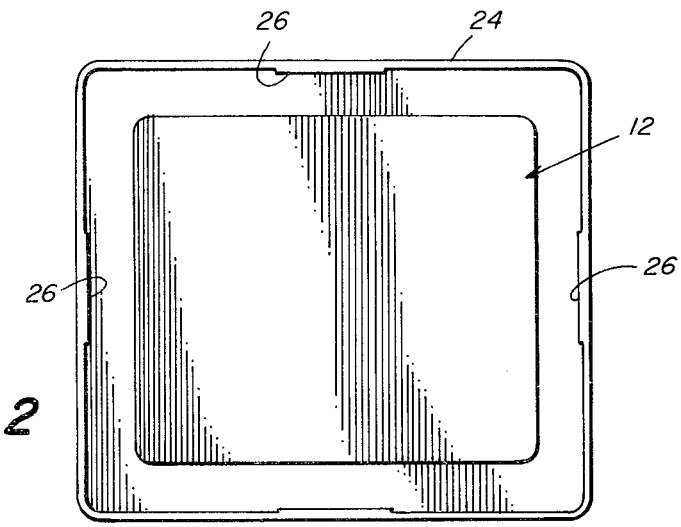
FIG. 2 is a bottom view.
Figure 3:
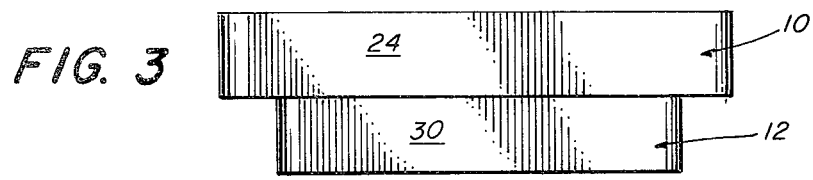
FIG. 3 is a side view.
Figure 4:
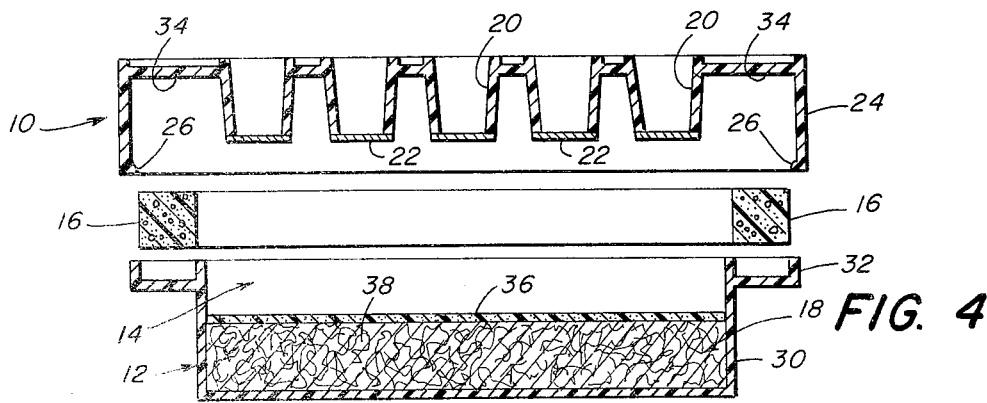
FIG. 4 is an exploded section on the line 4—4 of FIG. 1.

Referring to the drawing, the test device comprises a top member 10 telescoping with a base member 12 and defining therebetween a liquid reservoir 14, resilient means 16 such as resilient polyurethane foam or the like biasing members 10, 12 in the open position, and a sorbent material 18 in the reservoir 14.

Top member 10 is provided with a plurality of test wells 20, twenty-five as illustrated, each of which has a bottom opening covered by a microporous membrane 22 sealed liquid-tight to the circumference or periphery of the opening. Conveniently the top member is designed for molding of plastic such as polystyrene and the membranes can be sealed by any of a variety of known techniques, including heat sealing, solvent bonding to soften the styrene or by an adhesive. The top member 10 has a depending circumferential wall 24 provided with a plurality of small integral detents 26 at its lower margin adapted to snap over the outer edge of base member 12 to aid in retaining the members in assembled relation. If desired, detents 26 may be omitted, frictional fit and proper sizing of resilient foam 16 normally being sufficient to avoid disassembly in use.

Top member 10 is provided with air passage means such as a small hole 28 for expulsion and admission of air when the members are depressed and released to vary the volume of reservoir 14. Such means can be provided at any convenient location in or between the members and may be omitted, if desired, especially if the fit between the members is relatively loose. A snug fit with air passage means is preferred, however.

The membranes 22 are preferably of biologically inert materials and are thin and microporous, i.e., they have a multiplicity of interconnected pores of a size between about 25 nanometers and 25 micrometers, the pores occupying from about 60% to 80% of the membrane volume. Such membranes are well known and readily available in commerce. They have immobilized to their internal and external surfaces a coreactant for the reagent to be assayed in the test liquid samples. Such membranes with various biologically active materials immobilized thereto are disclosed in the previously cited U.S. Pat. No. 4,066,512. Any other suitable coreactant may be used and may be immobilized to the membrane in any suitable manner, including adhesion, cohesion, absorption, polymerization or the like.

Base member 12 comprises a depending portion 30 and an upper U-shaped circumferential lip 32 adapted to frictionally receive foam 16 which projects therefrom in position to contact the inside top portion 34 of member 10 when the members are squeezed or depressed from their open to their closed position. Sorbent material 18 is located in base member portion 30 and comprises a surface layer 36 and a bulk portion 38. Surface layer 36 is of a material which is substantially non-wetted by the liquids to be employed while bulk layer 38 is preferably wettable. For the normal aqueous liquids, top layer 36 may be of hydrophobic, porous non-woven rayon, for example grade 6212, 5 mils in thickness, 17.5 grams per square yard, of the Kendall Company, a material believed to be employed as the inner lining in disposable diapers. Bulk layer 38 is preferably an absorbent padding, for example, number 103 white saturating paper of the Hollingsworth and Vose Company. Sufficient thickness of material for layer 38 should be used to absorb all the liquids to be passed through the wells.

The above described device can be used to test a variety of liquids and reagent components by any suitable specific reaction procedure, for example chemical, immunochemical, enzymatic, catalytic, chromotographic or the like, in which one reagent may be in the test liquid and the other co-reactant immobilized or fixed to the membrane and at least one product of reaction retained in or on the membrane. However, the device is especially useful in immunochemical assays of the type described in the previously cited U.S. patent application, Ser. No. 751,099. As applied to assay of blood serum for antibodies to the antigens of *Toxoplasma gondii*, the following procedures may be employed.

Test devices having Toxoplasma antigens immobilized therein are provided, for example, as described in the above application. Other inert binder proteins such as dried bovine serum albumin can be used. Add 0.05 ml of test serum diluted 1:6 with Tris-saline buffer, pH 7.8 to 8.2, to one test well and a like quantity of positive and negative control to adjacent test wells to cover the membranes. Incubate at room temperature (20°–30° C.) for ten minutes and depress the cassette to pass the samples through the membranes into the sorbent material. Release when the membranes appear dry and fill the wells (0.8 ml) with aqueous Tris-saline wash buffer. Depress the cassette until the membranes appear dry and release. Carefully pipette 0.1 ml of enzyme-linked antibody, goat anti-human immunoglobulin linked with horseradish peroxidase as described in the above application, into each well to cover the membranes. Incubate for 15 minutes at room temperature. Depress the cassette until the membranes appear dry. Again wash with Tris-saline solution. Add 0.05 ml of substrate-chromogen stain solution, incubate for 5 minutes, and compare any color change present with the positive and negative controls. The stain solution may comprise in water 0.3 mg/ml 4-aminoantipyrine, 20 mg/ml sodium hydroxybenzoate, 16.6 mg/ml potassium phosphate, monobasic, and 34.8 mg/ml potassium phosphate, dibasic. Color development of the test well similar to the negative control is negative; similar to positive control is positive; and intermediate color, indeterminate, requiring other or additional tests.

It should be noted that the test requires only about 30 minutes, compared to hours for prior procedures, and no special laboratory equipment is required. The test may be performed at any suitable location in a laboratory or in the field. All materials and equipment may be conveniently packaged as a kit and used without special training or skill. In the absence of sorbent material and means for bringing it into contact with the lower surface of the membranes, it has been found that gravity alone is insufficient to cause the liquids to pass through the membranes. While useable in any convenient size, the test device of this invention is best adopted for testing small liquid quantities, preferably less than 10 ml, and most preferably less than one ml. Membrane filters about 10 mm diameter, Millipore Type SS, are preferred.

In addition to tests for antibodies to antigens of *Toxoplasma gondii*, the device may have immobilized to the membrane an antibody to Hepatitis B virus, an antibody or antigen to *Entameba histolytica*, Rubella antigen, nucleic acids, or human antiglobulins to test respectively for the corresponding antigens or antibodies or for measuring levels or types of globulins in serum.

It should be understood that the foregoing description is for the purpose of illustration and that the invention includes modifications and equivalents within the scope of the appended claims.

What is claimed is:

1. A test device for assaying a test liquid for the presence of a predetermined reactant by incubation with a coreactant therefor to form and wash a detectable reaction product, said device comprising:

top and bottom members disposed for relative movement toward and away from each other to define an open position and a closed position, means for biasing said members in the open position, at least one well for test liquid in the top member, said well having an open bottom, a microporous membrane having substantially uniform pores having between about 25 nanometers and 25 micrometers sealed liquid-tight to the periphery of and extending substantially horizontally across the open bottom of the well, said well or membrane containing or constituting said coreactant, and solid sorbent material carried by said bottom member, the major portion of said material being wettable by said liquid, the upper surface of said sorbent material being disposed for contact with the bottom of said membrane when the members are in the closed position but being removed therefrom in said open position, whereby liquid is retained in said well when the members are in the open position but flows through the membrane into the sorbent material in the closed position.

2. A test device according to claim 1 wherein said coreactant is a biologically active material immobilized to the surfaces of said membrane.

3. An immunochemical test device according to claim 2 wherein said reactant is an antibody or antigen and said coreactant is an antigen or antibody immunochemically binding to said reactant.

4. A self-contained, disposable test device according to claim 3 wherein said biasing means comprising a resilient material disposed between the members, one of the members fitting within the peripheral margin of the other and being disposed to telescope within said other in moving from the open to the closed position.

5. A device according to claim 3 wherein said immobilized coreactant is an antigen of *Toxoplasma gondii*, an antibody to Hepatitis B virus, an antibody to *Entomeba histolytica*, Rubella antigen, nucleic acids, or human antiglobulins.

6. A test device according to any one of claims 1 to 4 having a plurality of test wells in the top member, each of said wells having a bottom opening covered by a microporous membrane having said coreactant immobilized thereon, said membranes being substantially in a common plane.

7. A test device according to any one of claims 1 to 4 wherein said sorbent means comprises a porous top layer which is substantially non-wettable by the test liquid, and a lower bulk layer which is wettable by the test liquid, whereby plurality of liquids may be sequentially passed through the membranes without substantially re-wetting them with previously sorbed liquids.

8. A test device according to claim 7 wherein said device is portable, the test wells each have a fluid capacity less than about 10 milliliters, and said sorbent material has a capacity to sorb substantially all of the liquids to be passed through the membranes.

9. A test device according to claim 7 wherein said test liquid is aqueous and the surface layer of the sorbent means is a hydrophobic material.

10. A test device according to claim 7 wherein said microporous membrane is thin and comprises at least about 60% voids by volume.

11. The method of assaying for the presence of a predetermined reactant in a test liquid which comprises:
providing a test device according to any one of claims 1, 2, 3 or 4, the top and bottom members thereof being in the biased open position,
placing test liquid in said well and incubating for a time sufficient to form said reaction product,
moving said members toward each other from the open to the closed position and allowing the test liquid to flow through the membrane into the sorbent material,
moving said members away from each other to the open position,
adding a washing liquid to said well,
moving said members toward each other from the open to the closed position and allowing the washing liquid to flow through the membrane into the sorbent material, and
determining the presence or absence of said reaction product.

12. The method according to claim 11 wherein said reaction product is the combination of an antigen and antibody bound to the surfaces of the membrane, said reaction product being determined by adding to the well with the members in the open position an enzyme conjugate binding to said reaction product, passing unreacted conjugate through the membrane into the sorbent material by moving the members to the closed position, thereafter washing the membrane by adding washing liquid to the well and passing it into the sorbent material while holding the members in the closed position, moving the members to the open position, and adding to the well a chromogen solution which changes color in the presence of said enzyme.

* * * * *